United States Patent [19]

Schalkowsky

[11] Patent Number: 4,637,053
[45] Date of Patent: Jan. 13, 1987

[54] COMPUTER ASSISTED BIOLOGICAL ASSAY SYSTEM

[75] Inventor: Samuel Schalkowsky, Chevy Chase, Md.

[73] Assignee: Spiral System Instruments, Inc., Bethesda, Md.

[21] Appl. No.: 606,886

[22] Filed: May 3, 1984

[51] Int. Cl.⁴ .......................... G06K 9/00; C12Q 1/18
[52] U.S. Cl. .......................................... 382/6; 435/39; 435/291
[58] Field of Search ............... 382/6, 66, 68; 364/555, 364/557, 582, 416, 413; 356/39; 377/7, 10; 435/808, 291, 39, 32, 30

[56] References Cited

U.S. PATENT DOCUMENTS

3,799,844  3/1974  Campbell et al. .................... 435/292
3,892,632  7/1975  Campbell et al. .................... 435/808
3,962,040  6/1976  Campbell et al. .................... 435/291
4,353,988 10/1982  Couse et al. ......................... 435/291
4,517,292  5/1985  Schalkowsky et al. ............. 435/808

Primary Examiner—Stephen A. Kreitman
Attorney, Agent, or Firm—Antonelli, Terry & Wands

[57] ABSTRACT

The present invention is an improved system for counting of bacterial colonies on a plate. The system permits the counting of colonies under adverse colony counting conditions where there is overlap of colonies and analyzes the plate in a plurality of segments. The colony counts for each segment are subjected to count correction, size qualification and distribution qualification to correct for missed counts and to eliminate data from the system data base when the count for a segment will not produce reliable data. The entire plate is also analyzed for subsample qualification which provides the best estimate of the bacteria containing liquid which was used to produce the colonies as represented by a coefficient of variation of the bacterial density in the liquid.

16 Claims, 7 Drawing Figures

COMPUTER ASSISTED BIOLOGICAL ASSAY SYSTEM

BACKGROUND OF THE INVENTION

1. Field of the Invention

The present invention relates to systems for automated counting of visible bacterial colonies in culture media (agar plates). In addition, the invention relates to automated colony counting systems for accurate counting of colonies under adverse colony crowding conditions and which have ability to discriminate between different parts of the culture medium to permit selection of those regions which will produce the best available measurement of the bacterial concentration of the sample contained in or on the culture medium.

2. Description of the Prior Art

Automated bacterial colony counting systems are commercially available for determinng the number of visible bacterial colonies in or on a culture medium such as a Petri dish. In the preferred embodiment of the present invention, a prior art commercially available bacteria colony counting system, the Model 500A Laser Bacteria Colony Counting system, sold by Spiral System Instruments, Inc. of 4853 Cordell Avenue, Bethesda, Md. 20014, is used for providing raw counting data in the form of signals used for analysis of colonies with the present invention.

Various methods and apparatus for manually and automatically plating culture mediums with bacteria containing solutions are well known. U.S. Pat. Nos. 3,799,844, 3,892,632 and 3,962,040 disclose apparatus for plating bacteria containing solutions in a spiral. A commercially available instrument, known as the SPIRAL PLATER, which is manufactured under the aforementioned patents, can be programmed to deposit any desired volume of sample per unit length of the deposition path. The volume in any segment of a plate is determinable from knowledge of the control program deposition rate as a function of radial displacement of the dispensing stylus on the plate. Manual methods for applying bacteria containing solutions are exemplified by "pour" and "spread" plates. The visible colonies of the culture mediums produced by the aforementioned methods and apparatus are counted by either manual methods or an automated counting system as described in the above-referenced patents and commercially available Model 500A Laser Counter. Automated colony counting systems do not accurately distinguish overlapping colonies and, moreover, do not perform any analysis of the raw colony counts to eliminate the data of unreliable counts to increase reliablility of the assessment of bacterial concentration in the applied sample.

SUMMARY OF THE INVENTION

The present invention permits the accurate counting of colonies (as used herein colony means bacterial colony or other objects which may be detected by scanning with a scanning beam) under adverse colony crowding conditions where colonies are run together or overlap, and the subsequent analysis of the detected colonies in a plurality of separate segments within a subsample. The purpose of the analysis is to retain only the data from those segments that will produce the best available measurement of the CFU (colony forming units) per unit volume of the sample being assayed.

The invention performs a count correction of the number of colonies detected by the scanning spot in each segment of a subsample to correct for the number of colonies missed consequent to overlapping of colonies. The number of colonies is first detected by the scanning spot, the average size of the colonies which have been counted is determined and the corrected number of colonies is obtained as a function of the detected number of colonies, the computed average diameter and segment geometry. The count-correction procedure includes a test of the relationship between the parameters of the correction algorithm and the measured values to determine whether a valid correction is feasible and to disqualify the segment from use if acceptable reliability of count correction is not achievable.

A size qualification test is performed for the detected colonies of each segment of a subsample. The size qualification test functions to identify those segments in a subsample which have an average colony size which differs from the average of all of the segments in the subsample by a threshold value. The data in those segments which have an average size exceeding the threshold is excluded from further analysis in the system data base. Average colony size in a segment is determined from the number of first intercepts and either of the total number of times each colony is intercepted or the total number of colony counter clock pulses during interception.

A distribution qualification test is performed for the detected colonies of the segments within each subsample, preferrably after the count correction and size qualification tests described above are performed to eliminate unreliable data. It is known that the numerical distribution of colonies in equally sized segments of a culture medium approximates a Poisson frequency distribution. The numerical distribution of segment colonies within a subsample is analyzed to determine two coefficients of variation. One coefficient of variation is computed assuming a reference distribution (Poisson or other reference distribution) of all the colonies for the subsample. If the coefficient of variation which is next computed from all of the segment data is as good or better than the coefficient of variation for the assumed reference distribution, the data for all of the segments within the subsample is retained in the system data base. If the coefficient of variation computed for the segment data is not as good as the coefficient of variation is for the assumed reference distribution, individual segments are omitted, one at a time from the calculation of the coefficient of variation of the segment data to determine the effect of the omission of the segment on the comparison of the two coefficients of variation. If the effect causes the segment coefficient of variation to move closer to the coefficient of variation for the assumed reference distribution, the data for that segment is discarded. The above procedure is reiterated until either the segment calculated coefficient of variation equals or exceeds that of the reference distribution or the number of segments remaining is two at which point the qualification is discontinued.

A subsample qualification test is performed to provide the best estimate of the bacterial concentration in the liquid which was sampled to produce the colonies, as represented by a coefficient of variation for the colonies within all the segments whose data is retained in the system data base after the above-described count, size and distribution qualification analysis. The corrected colony counts of all the segments which remain after the above-described tests are completed are summed and divided by the sum of the corresponding sample volumes to provide an estimate of the number of CFU per unit volume of liquid sample used for preparing the plate (the volume of liquid sample deposited in each segment is available from program memory). An estimated coefficient of variation of the estimated number of colony forming units per unit volume of the material from which the sample was derived, is obtained as a function of (1) statistical variation assuming a Poisson distribution (which is computed from one divided by the square root of the total corrected count), (2) an additional component added to the calculation of (1) above to reflect departure from a Poisson distribution as determined from the subsample distribution qualification described above, and (3) a component of variation to account for estimated errors introduced by the count-correction procedure.

DESCRIPTION OF THE PREFERRED EMBODIMENTS

I. System Description

Figure 1:
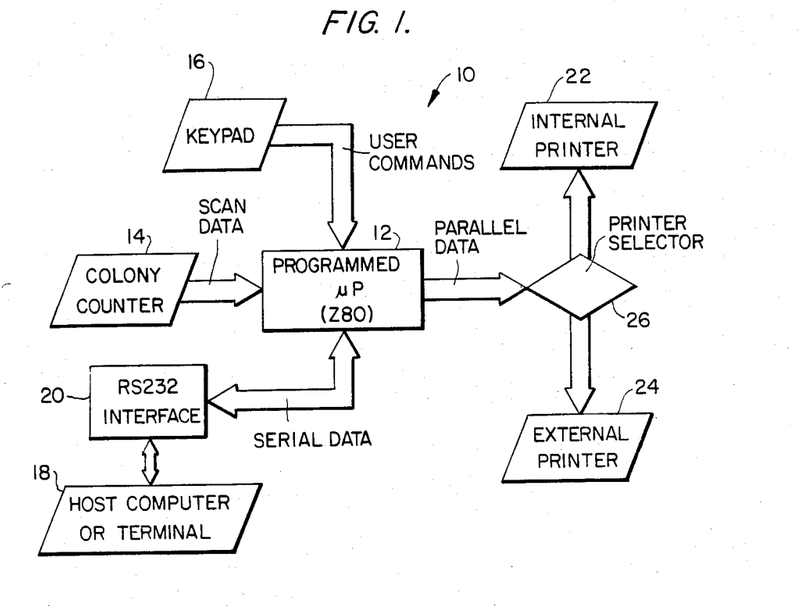
FIG. 1 is a schematic of the preferred form of the system for practicing the invention.
Figure 7:
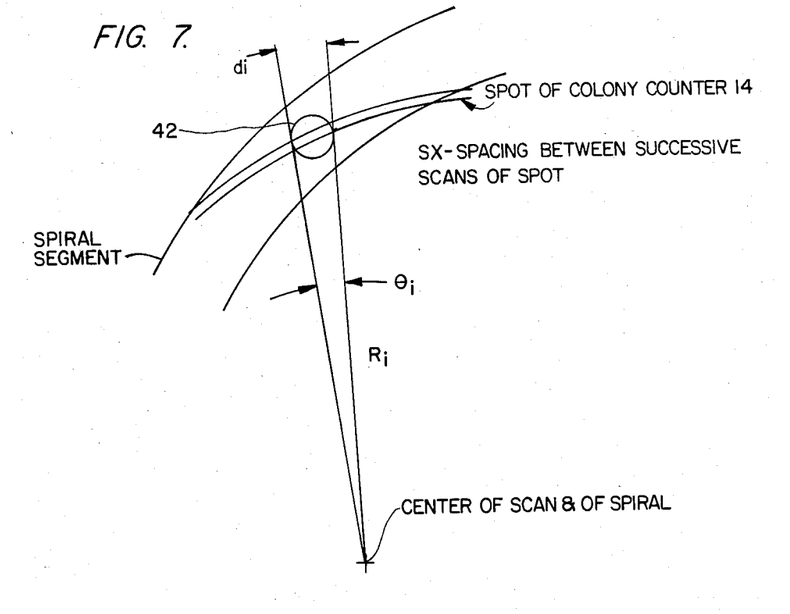
FIG. 7 illustrates the geometry of the scanning spot, spiral segment and colony during scanning by the colony counter.

FIG. 1 illustrates the preferred form of the system 10 used for the practice of the present invention. The overall system 10 is controlled by a programmed microprocessor 12 which controls the overall operation of input-output devices as well as the calculations of various quantities which permit the invention to accurately count colonies under adverse crowding conditions of colony overlap as well as identifying and eliminating data from the system data base of segments which contain unreliable colony counts to produce the best available measurement of the CFU per unit volume of the sample being assayed. The programmed microprocessor may be a Z80. A colony counter 14 is coupled to the programmed microprocessor to provide signals representative of various information involving the visible colonies (described below in FIGS. 3, 4 and 7) contained on the plate which is scanned by the colony counter. The preferred form of colony counter 14 is the Model 500A Laser Bacteria Colony Counter described above. An interface unit (not illustrated) is provided between the colony counter 14 and the programmed microprocessor 12 to accumulate data for readout to the programmed microprocessor on a synchronous basis with a signal produced by the Model 500A Colony Counter when a quadrant boundary (FIGS. 2 and 3) is being crossed. The Model 500A Colony Counter provides signal outputs of (1) the number of intercepts of the laser spot with colony boundaries (a colony is assumed present when 70% of the laser light is obscured), (2) the number of first intercepts with each colony (the laser scans a spiral path which progressively decreases in radius), (3) the number of colony counter clock pulses present during interception of the visible colonies with the spot and (4) the colony counter clock signal. Each of these four signals is used by the microprocessor in performing the functions described below. A keypad 16 provides a mechanism for entering user commands into the system. The system 10 may be coupled to a host computer 18 by means of a standard RS 232 interface for providing serial data communications. An internal printer 22 and an external printer 24 may be selectively coupled to the programmed microprocessor 12 by a parallel data path. The printer selection is accomplished by printer selector 26.

The present invention is not limited to any particular form of application of bacteria containing solutionsto produce visible colonies in a culture medium. Automated plating methods, as exemplified by U.S. Pat. Nos. 3,799,844, 3,892,632 and 3,962,040, as well as "pour" and "spread" plate methods may be used. When "pour" and "spread" methods are used, a uniform sample volume per unit area of the culture medium is assumed.

Figure 2:
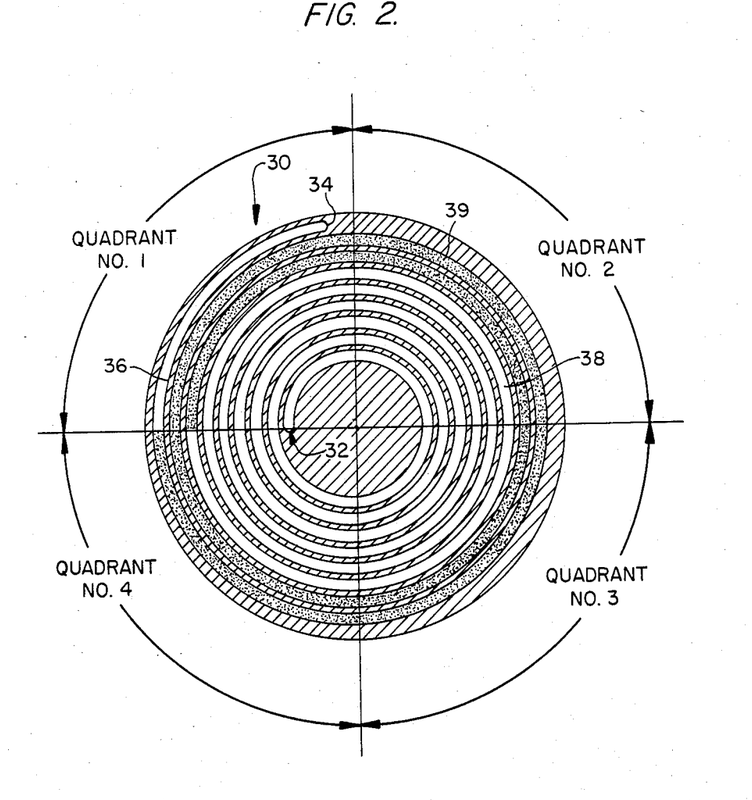
FIG. 2 illustrates a pattern of deposition of a liquid sample which may be used to produce a plate which is to be counted by the present invention.

FIG. 2 illustrates a spiral pattern 30 of deposition of a liquid sample which may be used to produce a plate which contains colonies to be counted by the present invention. The spiral pattern 30 has a plurality of turns beginning from an interior point 32 and ending at an exterior point 34. The cross hatching 36 identifies the part of the plate which is not contacted with the bacteria-containing solution. The spiral pattern 30 analyzed includes a plurality of subsamples (outermost subsample 39 is identified by stippling) which each consist of two complete turns adjacent (720 degrees) of the spiral 30 with the exception of the innermost spiral which can contain more or less than two complete turns, since analysis is started at an arbitrary quadrant boundary containing a full segment. Each subsample 39 includes eight segments 38 which each subtend 90 degrees of the plate (one quadrant) with the exception of the innermost segment which may contain fewer or more than eight segments.

Figure 3:
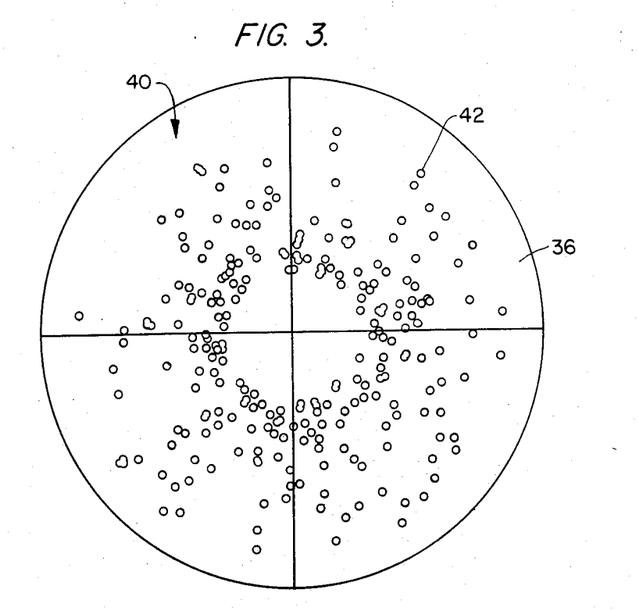
FIG. 3 illustrates a plate containing visible colonies prepared from the deposition pattern of FIG. 2 which are to be counted.

FIG. 3 illustrates an incubated plate 40 (culture medium) containing a plurality of colonies 42 which have been deposited with a SPIRAL PLATER manufactured by Spiral Systems, Inc., 6740 Clough Pike, Cincinnati, Ohio, 45244, under the aforementioned United States Patents. The SPIRAL PLATER applies an Archimedes spiral of the bacteria-containing solution (FIG. 2) in accordance with a programmed deposition rate (either fixed or variable per unit length of the spiral) which is incubated to produce the aforementioned visible colonies 42. As is apparent from inspection, a significant percentage of the colonies overlap which can produce inaccurate automated colony counting as a consequence of the inability of the colony counter 14 to accurately discriminate overlapping colonies as separate colonies. The analysis of the plate 40 is by counting the individual colonies 42 in a plurality of segments (FIG. 2) within the four quadrants (FIGS. 2 and 3) of the plate. Each segment 38 is defined by a specified number of scans of the spot scanner and subtends 90 degrees of the plate 28. The Model 500A colony counter scans the plate over 500 revolutions. The end of each quadrant is signalled by the generation of an end of quadrant signal generated by the colony counter 14. The analysis performed by the microprocessor 12 is on a segment basis for determining count correction, size qualification and distribution qualification as described hereinafter. All of the subsample data is analyzed in the subsample qualification routine described hereinafter.

II. Count Correction Algorithm

The count correction algorithm of the microprocessor corrects for missed colonies 42 consequent from colony crowding which makes accurate automated colony counting questionable. A corrected colony count is produced for each segment 32 for which reliable count-correction can be made.

Figure 4:
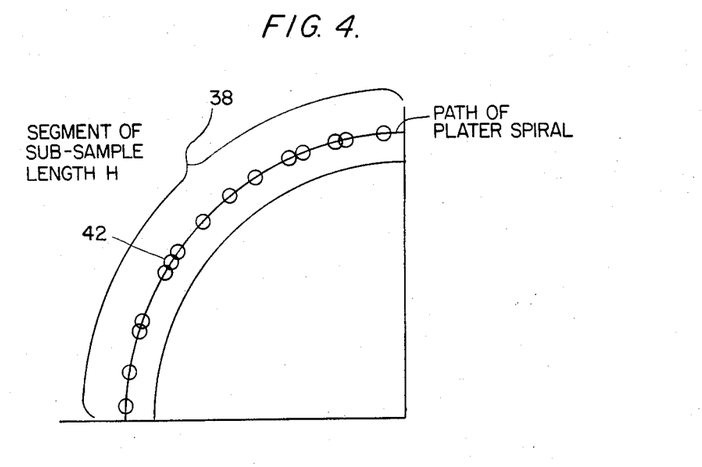
FIG. 4 illlustrates a single segment of a subsample illustrating colonies to be counted.

FIG. 4 illustrates a single segment 38 containing a plurality of visible colonies 42 including some overlapping colonies which make accurate colony counting difficult or impossible with the colony counter 14. Only a single segment of colonies 42 is shown to simplify the illustration. As illustrated, the spiral arc length of the segment 38 is represented by the parameter H in equations described hereinafter.

The following parameters are utilized.
H—Length of spiral arc of segment 38 being analyzed
CA—Actual number of colonies in a segment 38
C—Count obtained by colony counter 14
CM—Number of colonies missed by colony counter 14
The following mathematical relationship exists:

$$CA = C + CM \tag{1}$$

F is the fraction of CA missed $$F = \frac{CM}{CA} = \frac{CA - C}{CA} = 1 - \frac{C}{CA} \tag{1A}$$

The fraction missed is a function of:
(a) colony crowding = CA/H
(b) colony size, as measured by its diameter DA
(c) laser beam diameter, referred to as spot-size.

The procedure of defining the count-correction algorithm consists of preparing a set of plates at different bacterial concentrations using the uniform deposition rate cam of the SPIRAL PLATER. After incubation, the colony counter 14 (set at the smallest practical spot-size) produces the count C over a defined length H of the segment 38, along with a measurement of the average colony diameter DA as described hereinafter. This measurement is updated at intervals during incubation to obtain the count at increasing colony diameters as the colonies increase in diameter as a function of incubation time. The different concentrations provide different crowding values CA/H. The actual count, CA, in the measured region is obtained from visual counting.

Figure 5:
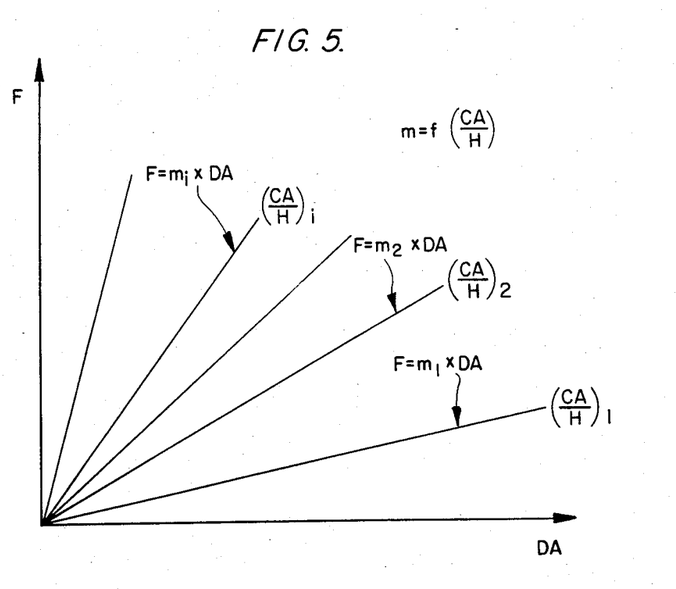
FIG. 5 is a graph of average colony diameter versus the fraction of missed colonies.

In the range of interest, a plot of F=CM/CA versus colony diameter DA produces essentially a straight line for a particular value of CA/H, representing data for a fixed bacterial concentration. As illustrated in FIG. 5, the slope of this line, m, is a function of CA/H.

Figure 6:
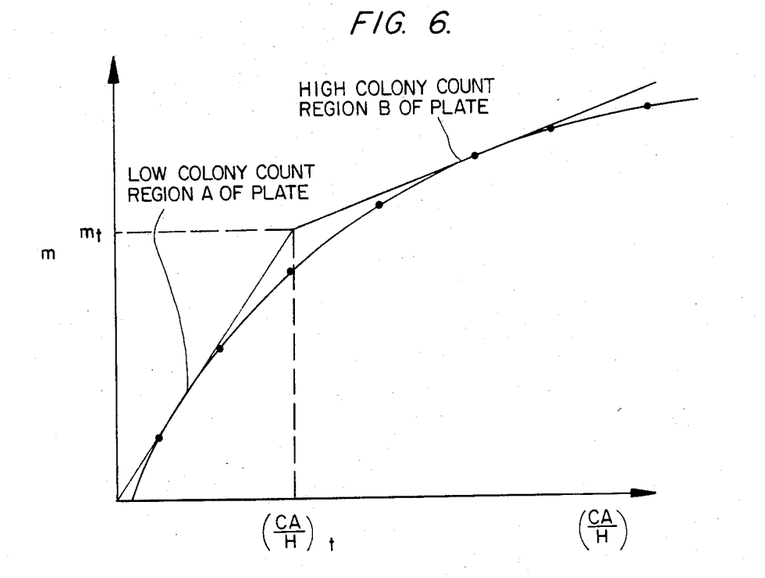
FIG. 6 is a graph of the number of colonies per length of the segment being analyzed (CA/H) versus the slope of the lines of FIG. 5.

The count correction algorithm is derived from the two relationships defined by FIGS. 5 and 6, viz.

$$F = 1 - \frac{C}{CA} = m \cdot DA \tag{2}$$

and $$m = \text{function of } \frac{CA}{H} \tag{3}$$

A convenient method for solving these equations is to make the piece-wise linear approximations shown in FIG. 6. The general straight line equation is:

$$m = A + B \cdot \left(\frac{CA}{H}\right) \tag{4}$$

With $(CA/H)_t$ and $m_t$ representing the transition point, the first, low crowding region A is approximated by $$m = B_1 \cdot \frac{CA}{H} \text{ since } A_1 = 0 \tag{5}$$

and is valid for $$\frac{CA}{H} \leq \left(\frac{CA}{H}\right)_t \tag{5}$$

while the second is given by $$m = A_2 + B_2 \cdot \left(\frac{CA}{H}\right) \tag{6}$$

and is valid for $$\frac{CA}{H} > \frac{CA}{H}_t$$

Combining equation 1 and 3, $$1 - \frac{C}{CA} = \left[A + B\left(\frac{CA}{H}\right)\right] \cdot DA \tag{7}$$

which is rearranged to facilitate a solution for CA as $$\left(\frac{B \cdot DA}{H}\right) \cdot CA^2 + (A \cdot DA - 1) \cdot CA + C = 0 \tag{8}$$

The solution for CA in accordance with the quadratic formula is:

$$CA = \frac{(1 - A \cdot DA) \pm \sqrt{(1 - A \cdot DA)^2 - 4 \cdot B \cdot DA \cdot C/H}}{2 \cdot B \cdot DA / H} \tag{9}$$

Let $$XB = 1 - A \cdot DA \text{ and } XF = B \cdot 2 \cdot DA \cdot \frac{C}{H}$$

and dividing both sides of equation 8 by C, equation 8 can be rewritten as:

$$CA = C \cdot \frac{XB - \sqrt{XB^2 - 2 \cdot XF}}{XF} \tag{10}$$

Only the minus sign in the ±part of equation 9 has actual meaning in this application.

The count correction algorithm thus consists of solving for the actual count, CA, using equation 10 in conjunction with equation 9. The coefficients A and B are known from the experimental data of FIG. 5 for the two linear approximation regions. C is the count provided by the colony counter 14 and H is known from the geometry of the spiral as illustrated in FIG. 4.

Referring to equation 10, since the square root cannot be negative $$XB^2 - 2 \cdot XF \geq 0 \tag{11}$$

or $$XF \leq \tfrac{1}{2} \cdot XB^2 \tag{12}$$

Equation 11 provides a basis for disqualifying a segment. For example, in the initial, low-crowding region of FIG. 5 where $XB=1$ (since $A=0$, See equation 9), XF must be less than or equal to 0.5. When $XF=0.5$, equation 11 yields $CA = 2 \times C$, i.e., the count-correction procedure stops, in this case, when the estimated actual number of colonies is twice that counted by the colony counter 14, otherwise a negative square root will result.

The count-correction model parameter values are obtained from experimental data using a fixed spot-size, e.g., the smallest spot diameter which can be used without producing too many extraneous counts. The effect of other spot-size settings could be accounted for by repeating the measurements at various settings and defining the model parameters as a function of spot-size.

A simpler, but adequate approach is to define the model only in terms of one low spot-size setting and computing the plate CFU per unit volume value on this basis. This value can then be adjusted to account for the fact that the number of missed counts was somewhat larger with the larger spot-sizes and the estimated bacterial concentration should therefore be adjusted upward.

The bacterial enumeration program uses this approach. It multiplies the computed colony forming units per unit volume value based on a spot-size of 0.25 mm by the expression $$1 + KO \cdot FM \cdot (SZ - 0.25) \tag{20}$$

where

KO is a constant selected to represent the effect of spot-sizes other than 0.25 mm.

FM is the missed fraction of colonies for all the segments used in the analysis $$F = \frac{\Sigma CA - \Sigma C}{\Sigma CA}$$

SZ is actual spot-size used in mm.

Example of Count-Correction Procedure

For a given equipment design, the values of A and B for the two regions of FIG. 6 will have fixed values which, in turn, would produce the following typical relationships for their respective XB's and XF's:

$$XB_1 = 1$$

$$XF_1 = 1.6 \cdot DA \cdot C/H$$

$$XB_2 = 1 - 0.11 \cdot DA$$

$$XF_2 = 0.7 \cdot DA \cdot C/H$$

Transition from region 1 to region 2 of FIG. 6 occures at $CA/H = 0.20$.

Consider a particular segment having a length $H = 50$ mm, determined from its location on the plate and a knowledge of the spiral geometry. The following table shows the typical situations which can be encountered in determining the corrected count, CA, from the laser count, C, and computed average colony diameter, DA, of the segment.

| | 1<br>C | 2<br>C/H | 3<br>REGION | 4<br>DA | 5<br>XB | 6<br>XF | 7<br>$XB^2 - 2XF$ | 8<br>CA | 9<br>CA/H |
|---|---|---|---|---|---|---|---|---|---|
| 1 | 8 | 0.16 | 1 | 0.5 | 1 | 0.128 | 0.744 > 0 | 8.59 | .17 |
| 2 | 9 | 0.18 | 1 | 1.0 | 1 | 0.288 | 0.424 > 0 | 10.9 | .218 |
| 2a | | | 2 | | 0.89 | 0.126 | 0.54 > 0 | 11.08 | — |
| 3 | 25 | 0.5 | 2 | 1.5 | 0.835 | 0.525 | −0.35 < 0 | N.C. | — |

Since CA is not known when starting the computation, the determination of which region applies is first made on the basis of C/H rather than CA/H. If C/H is larger than the transition value of $CA/H = 0.2$, then region 2 would apply since $CA \geq C$.

Row 1 above illustrates the computation when region 1 is used because $C/H < 0.2$. After CA is computed on this basis, CA/H is computed and, in this case, remains smaller than the transition value of 0.2. Row 2 shows the case where the computation was initially based on region 1 but was found to be in region 2 after CA was computed. The computation is therefore repeated using region 2 parameters (see ROW 2a) resulting in a CA value of 11.08.

Row 3 shows the case where the square root test of column 7 yields a negative value, leading to a "not countable" (N.C.) decision and consequent disqualification of the segment.

III. Colony Size Determination

Two alternate procedures may be used for the computation of the colony diameter which are based either on an area analysis or an intercept analysis.

A. Area Basis

The area basis for calculating colony size is based on computation of area and the number of colonies in the segment 38 which number is available from the colony counter 14. From FIG. 7, the area covered over all of the colonies 42 in the i-th scan of the colony counter 14 is $$A_i = \Sigma d_i \times SX \tag{12A}$$

Since there are 256 pulses provided by the colony counter clock during the counter scan of a segment 38, corresponding to $(2\pi Ri/4)$ radians of rotation, and denoting by $L_i$, the actual number of intercepted pulses during the scan of a segment 32, $$\frac{L_i}{256} = \frac{\Sigma d_i}{2\pi R_i/4} \tag{13}$$

From 12A and 13, $$A_i = \Sigma d_i \times SX = \frac{2\pi}{4 \cdot 256} \cdot L_i R_i \cdot SX \tag{14}$$

The total area of intercepted colonies 42 in the spiral segment 38 is obtained from summing the $A_i$'s over all the scans covering the segment $$AI = \Sigma A_i = \frac{\pi}{512} SX \cdot \overset{i}{\Sigma} L_i R_i \tag{15}$$

The actual number of colonies 42 in the segment 38 is CA. Thus, the actual average colony diameter, D, is obtained from $$\frac{\pi}{4} D^2 \cdot CA = AI \tag{16}$$

$$D = \left[ \frac{AI}{CA} \cdot \frac{4}{\pi} \right]^{\frac{1}{2}} \tag{17}$$

In practice, CA is not known when the computation for D is being made. Therefore, the laser count, C, must be used to obtain the estimated diameter DA.

$$DA = \left[ \frac{4}{\pi} \cdot \frac{AI}{C} \right]^{\frac{1}{2}} \tag{18}$$

It is important to note that the use of C rather than CA is not a serious limitation because when C<CA, i.e. there are missed counts, which is caused by overlapping colonies 42. But overlap also produces a smaller measured area, AI. Since AI is in the numerator and C in the denominator, they compensate for each other to yield adequate accuracy as long as the calculation is not done in overly crowded regions.

The area basis of DA has the feature that, as more and more crowding occurs, DA tends to become bigger than the true value, since C<<CA. It has the disadvantage that, since the number of clock pulses from colony counter 14 is the same in each scan, regardless of the radius of the scan, the measurement becomes less sensitive at large radii.

Area based DA is preferably not used for count-correction. It is, however, well suited for testing the first subsample to see if the plate is too crowded for analysis. Specifically, when the number of segments which pass the count-correction qualification procedure, with DA computed on an area basis, is less than 3, the plate is considered "NOT COUNTABLE", since all subsequent subsamples of a plate made with a variable program deposition rate cam are expected to be more crowded than the first subsample for the reason that the concentration of bacterial deposition increases as a function of decreasing radius.

B. Intercept Basis of Colony Diameter Measurement

On each scan of the spot of the colony counter 14, the number of times colonies are intercepted is accumulated and stored in microprocessor memory. The sum of all of these intercepts NI over a spiral segment 38 can therefore be used to compute the average colony diameter from the equation $$D = \frac{NI \cdot SX}{CA} \tag{19}$$

wherein SX=radial advance between laser scans.

Again, CA is not available and C is used instead to provide $DA = NI \times SX/C$. In this case also there is a compensating effect between the reduction in the number of measured intercepts because of colony overlaps and the fact that C<CA because of these overlaps.

The computation should also account for the fact that the first intercept may not represent a full scan advance, depending upon the threshold setting for detecting an obstruction defined in the colony counter 14. A more complete equation for intercept-based diameter computation is:

$$D = \frac{NI \cdot SX}{C - 1} + KS \cdot SZ$$

where SZ is the spot-size and KS is a constant dependent upon the counter detection threshold.

The intercept basis calculation is not dependent on location, i.e., the value of R, and therefore has uniform sensitivity over the entire plate. It is therefore used for computing DA in the count-correction algorithm.

IV. Size Qualification

Analysis of relative colony size amongst the various segments of a sub-sample serves to identify segments containing geometrical anomalies, such as may be due to the presence of a large mold which obscures a number of the colonies of interest.

The procedure is to compute the mean colony size of the average colony diameter of all the segments and to compare the individual segment diameter to this overall mean. If the individual segment colony size differs from the mean by a selected amount, the segment is disqualified and its data removed from the data base.

Example of Size Qualification Procedure

Assume that a subsample has 5 remaining segments after the count correction procedure was applied to the initial 8 segments of the subsample. Further assume that the average colony size in each of these segments is as shown below:

| Segment | Diameter-mm |
|---|---|
| 1 | 0.90 |
| 2 | 1.30 |
| 3 | 0.86 |
| 4 | 0.92 |
| 5 | 1.45 > 1.303 Disqualified |

Mean Segment Diameter=1.086
1.2×Mean Diameter=1.303

If it is decided that any segment whose average colony size exceeds the mean of all the segment sizes by 20%, then segment number 5 would be disqualified because 1.45>1.086×1.2.

V. Distribution Qualification

It is known that distribution of bacteria in a liquid sample frequently follows a Poisson distribution. Therefore, variation from a Poisson distribution indicates abnormal conditions.

Segment qualification for conformance to the Poisson distribution relies upon a comparison of coefficients of variation, CV, wherein $$CV = \frac{\text{standard deviation}}{\text{mean}} \quad (21)$$

Let:

N = Number of segments 38 in the subsample which survived the prior count-correction and colony size tests $CN_i$ = Concentration computed for any segment $$CN_i = \frac{CA_i}{V_i} \quad (22)$$

$V_i$ = Volume deposited in the i-th segment (Available from sample deposition apparatus and stored in memory)

$$VT = V_1 + V_2 + \ldots V_i + \ldots V_N \quad (23)$$

$$XS = CN_1 + CN_2 + \ldots CN_i + \ldots CN_N \quad (24)$$

$$X2S = CN_1^2 + CN_2^2 + \ldots CN_i^2 + CN_N^2 \quad (25)$$

In general, the coefficient of variation $CV_p$ for a sample containing CP colonies which follow the Poisson distribution is given by $$CV_p = \frac{\sqrt{CP}}{CP} = \frac{1}{\sqrt{CP}} \quad (26)$$

Since the volumes in the various segments are not equal, an average count per segment must be used for CP, viz:

$$CP = \frac{XS}{N} \cdot \frac{VT}{N} \quad (27)$$

Considering the N segments as individual measurements, their coefficient of variation, $CV_s$, is computed from standard formulae, viz.

$$\text{Std. Deviation} = \left[ \frac{X2S - XS^2/N}{N - 1} \right]^{\frac{1}{2}} \quad (28)$$

$$\text{Mean} = \frac{XS}{N} \quad (29)$$

E, the subsample quality, is defined as the ratio of the two coefficients of variations:

$$E = \frac{CV_p}{CV_s} \quad (30)$$

which is obtained from equations (26) through (29):

$$E = \left[ \frac{(N - 1) \cdot XS}{VT \cdot (X2S - XS^2/N)} \right]^{\frac{1}{2}} \quad (31)$$

If $E \geq 1$, then the distribution of colonies in the various N segments of the subsample are judged to conform to the desired Poisson distribution. If it is less than 1, those segments which contribute to non-Poisson distribution should be disqualified. This is accomplished by excluding one segment at a time and recomputing E, i.e. XS, X2S and VT are reduced by subtracting out the $XS_i$, $X2S_i$ and $V_i$ respectively for the i-th segment being evaluated and recomputing E with N also reduced by 1. If the new value of E is significantly larger than the reference E, initially computed, then the segment is disqualified.

The above procedure is continued until either a value of $E \geq 1$ is obtained or only two segments remain in the subsample.

The value of E at the conclusion of subsample qualification may still be less than 1, denoting less than optimum quality. This information is utilized in evaluating the relative usefulness of different subsamples.

Example of Poisson Qualification

The table below illustrates the procedure and computations involved in testing the 5 segments of a subsample which survived the preceding count-correction and size qualification tests, to see whether the inclusion of each of them is desirable from the point of view of achieving as close to a Poisson distribution of the colonies in the sub-sample as is practical.

| SEGMENT NO. | A V | B CA | C CN = CA/V | SEGMENTS TESTED | | | | |
|---|---|---|---|---|---|---|---|---|
| | | | | 1 | 2 | 3 | 4 | 5 |
| 1 | 0.154 | 10 | 64.94 | − | + | + | + | + |
| 2 | 0.162 | 25 | 154.32 | + | − | + | + | + |
| 3 | 0.170 | 13 | 76.47 | + | + | − | + | + |
| 4 | 0.178 | 16 | 89.89 | + | + | + | − | + |
| 5 | 0.186 | 3 | 16.13 | + | + | + | + | − |
| XS = ΣCN | | | 401.75 | 336.81 | 247.43 | 325.28 | 311.86 | 385.62 |
| X2S = ΣCN² | | | 42,220 | 38,003 | 18,405 | 36,372 | 34,139 | 41,960 |
| VT = ΣV | | | 0.850 | 0.696 | 0.688 | 0.680 | 0.672 | 0.664 |
| E | | | 0.436 | 0.388 | 0.60 | 0.380 | 0.376 | .604 |
| Qualification: | | | | + | − | + | + | − |

Column A lists the known volumes deposited in each of the segments, while column B summarizes the corrected counts obtained for each. Column C is the bacterial concentration computed for each segment by dividing column B by column A values.

The quality measure E, defined by equation 32, is first computed using the data for all 5 segments (N=5) and is found, in this case, to be 0.436. Since this is less than 1, segment qualification for distribution anomalies is desirable.

The "Segments Tested" part of the table shows the manner in which values of XS, X2S and VT are decreased by the individual values of CN, CN² and V, respectively, of the segment being tested. The value of E is then recomputed using equation 31 with N=4 to reflect the fact that one segment has been omitted. The value of E is found to be 0.388, indicating that the absence of segment 1 made things worse since 0.388 is smaller than the original value of E=0.436. This segment will therefore be retained.

In contrast to the above, the same procedure applied to segments 2 and 5 shows an improvement in each case since the computed values of 0.60 and 0.604 are now larger than the original E=0.436. These two segments are therefore rejected.

The final step is to compute a new value of E without the data of segments 2 and 5, which yields E=1.72, indicating a distribution comparable to that of a Poisson distribution (E≧1).

In the above illustration, the Poisson qualification procedure eliminated the two segments with extreme values of concentraton CN. This will not, however, always be the case as distributional anomalies can be contriubted by segments which are not at the high or low end of the CN values.

VI. Subsample Qualification

The purpose of subsample qualification is to further select amongst the previously qualified segments so as to assure the best available correlation between the CFU per unit volume value computed from segment data and the bacterial concentration of the source material from which the sample deposited on the plate was derived. The procedure involves the iterative evaluation of a plate coefficient of variation at the conclusion of subsample segment qualifications (for count-correction, size and distribution) to determine whether or not the inclusion of the last subsample yielded an improvement or degradation of the plate coefficient of variation. If it was degraded, the last subsample is disqualified and all of its previously qualified segment data is excluded from the data base, and vice versa. The analysis then proceeds to the next subsample for segment qualification and then for a recomputation of the plate coefficient of variation.

It is to be noted that whereas the coefficients of variations defined for segment distribution qualifications dealt with the reliability of segment data in the context of colony distribution in the subsample on the plate, the plate coefficient of variation deals with the question of how reliably the data obtained from the entire plate defines the actual bacterial concentration in the source material from which the sample deposited on the plate was obtained.

One source of variability in relating the estimated CFU per unit volume, e.g. CFU/ML as obtained from segment data, to the source CFU per unit volume, is the total number of colonies used in computing the plate CFU/ML value, i.e. the sum of all corrected counts in the qualified segments, which equals $\Sigma CA_i$. If all subsamples used in the analysis had a value of $E \geq 1$, i.e. there were no distributional anomalies in the data used, the $\Sigma CA$ can be assumed to have followed a Poisson distribution. As previously noted, the coefficient of variation for a Poisson distribution as a function of the number of colonies used in the computation is given by $$CV_p = \frac{\sqrt{\Sigma CA_i}}{CA_i} \tag{26}$$

Some of the subsamples may, however, have shown a deviation from a Poisson distribution, ending with a value of E less than 1. The statistical variation component of the plate coefficient of variation must therefore be modified to reflect this additional source of variation. This can, for example, be done by computing a weighted coefficient of variation component for each subsample and summing these components to obtain their accumulated value, denoted here as $CV_1$:

$$CV_1 = \frac{\sqrt{CA_2/E_1^2 + \ldots + CA_i/E_2^2 + \ldots + CA_s/E_s^2}}{\Sigma CA} \tag{27}$$

$$CV_1 = \frac{\sqrt{\Sigma(CA_i/E_i^2)}}{\Sigma CA} \tag{28}$$

An additional source of variation, and therefore also a contributor to the plate coefficient of variation, is the error associated with estimating the number of missed colonies in the count-correction procedure. For a given design, this error effect could be evaluated from test data. It can also be estimated by a simple linear relationship based upon the expectation that the error will increase as the fraction of missed counts increases. Denoting by $CV_2$ the count-correction contribution to the plate coefficient of variation, it can be defined as, $$CV_2 = KM \cdot \Sigma CM / \Sigma CA \tag{29}$$

where KM is a proportionality constant and $\Sigma CM$ is the sum of the missed counts in all the qualified segments from which $\Sigma CA$ was obtained.

The total plate coefficient of variation is then the sum of $CV_1$ and $CV_2$:

$$CV = \frac{\sqrt{\Sigma(CA_i/E_i)}}{\Sigma CA} + KM \cdot \frac{\Sigma CM}{\Sigma CA} \tag{30}$$

The use of the plate coefficient of variation to qualify subsamples is illustrated in the table below using a value of KM=0.25

| SUB-SAMPLE NO. | CA | E | A = CA/E² | ΣA | ΣCA | CV₁ = ΣA/ΣCA | CM | ΣCM | CV₂ = KM·ΣCM/ΣCA | CV = CV₁ + CV₂ |
|---|---|---|---|---|---|---|---|---|---|---|
| 1 | 28 | 0.95 | 31.03 | 31.03 | 28 | 0.20 | 3 | 3 | 0.03 | 0.23 |
| 2 | 60 | 1.0 | 60 | 91.03 | 88 | 0.11 | 12 | 15 | 0.04 | 0.15 |
| 3 | (75) | (0.70) | (153) | (244.1) | (163) | (0.10) | (25) | (40) | (0.06) | (0.16) |

-continued

| SUB-SAMPLE NO. | CA | E | A = CA/E² | ΣA | ΣCA | CV₁ = ΣA/ΣCA | CM | ΣCM | $CV_2 = KM \cdot \frac{\Sigma CM}{\Sigma CA}$ | CV = CV₁ + CV₂ |
|---|---|---|---|---|---|---|---|---|---|---|
| 4 | 120 | 1.0 | 120 | 211.03 | 208 | 0.07 | 28 | 43 | 0.05 | 0.12 |

At the conclusion of subsample number 1, a CV value of 0.23 is obtained, reflecting the low number of colonies used (CA=28) so far, which yields a relatively high coefficient of variation; the contribution of $CV_2$ is not yet significant since the low number of colonies in the initial, uncrowded part of the plate also does not lead to count-correction errors.

In subsample 2, statistical variation is significantly reduced (from 0.20 to 0.11) because an additional 60 colonies were added. Also, crowding has not yet increased significantly ($CV_2$ remains about the same) and the coefficient of variation representing the use of the first two subsamples is therefore significantly better than that of subsample number 1 above. Subsample number 2 would therefore be incorporated in the data base.

Subsample number 3 shows poor distribution, since E=0.7, as well as increased count-correction error, due to increased crowding and, possibly, also due the distribution anomalies which may have generated larger than average colony size. Since the value of CV=0.16, computed on the basis of including subsample number 3, is greater than the CV=0.15 available at the end of subsample number 2, subsample number 3 would be disqualified and its data excluded from the data base.

The summations used for computing the coefficient of variation for subsample number 4 exclude the data (shown in parenthesis) of subsample number 3. Since its value of CV=0.12 is smaller than the CV=0.15 available without the use of subsample number 4, this subsample would be included in the analysis.

Upon completion of the analysis of the plate, a final CFU per unit volume is obtained by dividing the sum of the corrected counts in all the qualified segments of the qualified subsamples, into the sum of sample volumes deposited in these segments. The latter volume information is stored in the program, preferably in the form of an equation which relates deposited volume to length and location of any segment under consideration. The parameters of such an equation are known from the design of the plater which controls the sample deposition rate as a function of position on the plate.

The final value of the plate coefficient of variation serves to indicate how reliably the reported value of CFU/unit volume obtained from plate analysis represents the mean bacterial concentration of the source material from which the sample was obtained.

The average value of E for the subsamples used in the analysis serves to indicate to what extent anomalous conditions on the plate were used in arriving at the reported CFU/unit volume value.

It should be understood that the programming of the equations used for implementing count correction, size qualification, distribution qualification and subsample qualification is a matter of routine skill which is not part of the present invention.

While the count correction, size qualification and distribution qualification algorithms are implementable as independent routines of the microprocessor 12, the preferred embodiment of the invention implements these routines in the order as described to eliminate the effects of unreliable colony counts from the system data base.

While the invention has been described in terms of its preferred embodiment, it should be understood that numerous embodiments may be made without departing from the spirit and scope of the invention as defined in the appended claims.

I claim:

1. In a system for counting the number of colonies in a segment of an area by scanning the area with a scanning spot, a method for determining the number of counts missed because of colony overlap to produce a corrected count indicative of the actual number of colonies in the segment comprising:
    (a) scanning the segment with the scanning spot to determine a number of distinct colonies within the segment;
    (b) determining the average diameter of the scanned colonies; and
    (c) calculating the corrected count of colonies within the segment as a function of the sensed number of distinct colonies, the computed average diameter and segment geometry.

2. A method in accordance with claim 1 wherein the data of the segment is discarded when the calculation of a corrected count is mathematically impossible.

3. A method in accordance with claim 1 wherein the data of the segment is discarded when a predetermined condition is determined to exist.

4. In a system for counting the number of colonies in a plurality of segments of an area by scanning the area with a scanning spot scanner, a method for comparing average colony size in each individual segment to the average of all of the segments and for qualifying individual segments in accordance with the average size of the colonies contained in relationship to the average size of all of the colonies contained in the plurality of segments comprising:
    (a) scanning the plurality of segments with the scanning spot to detect the first intercepts of the scanning spot with each of the visible colonies of each segment during the scanning of the segments to permit determination of the number of distinct colonies in each segment; and
    (b) determining average colony size in each segment from said number of distinct colonies in each segment and a total number of intercepts in each segment.

5. A method in accordance with claim 4 wherein the average size of the colonies in all of the segments is computed from the average size of the colonies in each segment and the average size of the colonies in each segment is compared to the aerage colony size of all of the segments.

6. A method in accordance with claim 4 wherein the determining of average colony size also utilizes parameters derived from scan geometry of the scanning of the plurality of segments with the scanning spot.

7. In a system for counting the number of colonies in a plurality of segments of an area by scanning the area with a scanning spot scanner, a method for comparing average colony size in each individual segment to the average of all of the segments and for qualifying individual segments in accordance with the average size of the colonies contained in relationship to the average size of all of the colonies contained in the plurality of segments comprising:

(a) scanning the plurality of segments with the scanning spot to the first intercepts of the scanning spot with the visibile colonies of each segment during the scanning of the segments to permit determination of the of distinct colonies in each segment; and determining average colony size in each segment from said number distinct colonies and a total number clock pulses occurring during interception of the within each segment.

8. A method in accordance with claim 7 wherein the average size of colonies in all of the segments is computed from the size of the colonies in each segment and the size of the colonies in each segment is compared to the average colony size of all of the segments.

9. A method in accordance with claim 7 wherein the determining of average colony size also utilizes parameters derived from scan geometry of the scanning of the plurality of segments with the scanning spot.

10. In a system for counting the number of colonies in a plurality of segments in a subsample scanned by a scanning spot, a method for detecting deviation of the distribution of colonies in a subsample with respect to a reference distribution comprising:

(a) detecting the number of discrete colonies in each of the plurality of segments within the subsample;
(b) normalizing the segments as a function of liquid sample volume deposited in each segment;
(c) computing a coefficient of variation for the normalized segments of the subsample;
(d) computing a coefficient of variation for the reference distribution; and
(e) comparing the coefficient of variation for the normalized segments of the subsample with the coefficient of variation of the reference distribution to determine if the colonies in the subsample conform to the reference distribution.

11. A method in accordance with claim 10 wherein if the coefficient of variation of the subsample does not conform to that of the reference distribution, the data of individual segments is removed from the computation of the coefficient of variation of the subsample to produce a newly computed coefficient of variation of the subsample and the newly computed coefficient of variation is compared with the coefficient of variation of the reference distribution to determine whether better conformance to the reference distribution is achieved by the absence of the excluded data.

12. A method in accordance with claim 11 wherein the effect of each segment within the subsample in computation of the coefficient of variation of the subsample is determined and the removal of those segments which produce better conformance is performed until either acceptable conformance to the reference distribution is obtained or the effect of the removal of all but a predetermined remaining number of segments.

13. In a system for counting colonies in a plurality of subsamples which each contain a plurality of segments by scanning the subsamples with a scanning spot, a method for estimating the bacterial concentration in the sample used for producing the scanned colonies and providing an assessment of how well the estimated concentration for the sample represents the true concentration from which the sample was derived comprising:

(a) performing count correction, size qualification and distribution qualification for each segment within each subsample to produce a total corrected count for all of the segments of the subsamples, a measure of the quality of the subsample as represented by the degree of conformance to a reference distribution and a determination of the proportion of the counts added by the correction procedure to the corrected count;
(b) determining the estimated bacterial concentration of the sample from the total count and the total volume contained in the segments which remain after count correction, size qualification and distribution qualification; and
(c) determining the measure of the conformance of the estimated concentration of the bacteria in the subsample to the bacterial concentration in a substance from which the sample was derived by calculation of an estimated coefficient of variation comprising a component due to statistical variation assuming that the corrected count of the subsample follows the distribution of the bacteria in the source, modifying the component due to statistical variation by the quality measure of the subsample obtained from the distribution qualification and a component associated with the fraction of the total corrected count derived from the count correction procedure.

14. In a system for counting the number of colonies in a plurality of segments of an area by scanning the area with a scanning spot, a method for comparing average colony size in each individual segment to the average of all of the segments and for qualifying individual segments in accordance with the average size of the colonies contained in relationship to the average size of all of the colonies contained in the plurality of segments comprising:

(a) scanning the segment with the scanning spot to determine a number of distinct colonies within the segment; and
(b) determining average colony size in each segment from said number of distinct colonies in each segment and a total number of intercepts in each segment.

15. In a system for counting colonies in a plurality of subsamples which each contain a plurality of segments by scanning the subsamples with a scanning spot, a method for estimating the bacerial concentration in a deposited sample used for producing the scanned colonies and providing an assessment of how well the estimated concentration for the sample represents the true concentration from which the sample was derived comprising:

(a) performing count correction, size qualification and distribution qualification for each segment within each subsample to produce a total corrected count for all of the segments of the subsamples, a measure of the quality of the subsample as represented by the degree of conformance to a reference distribution and a determination of the proportion of the counts added by the correction procedure to the corrected count;
(b) determining the estimated bacterial concentration of the sample from the total count and the total volume contained in the segments which remain after count correction, size qualification and distribution qualification; and (c) determining the measure of the conformance of the estimated concentration of the bacteria in the subsample to the bacterial concentration in a substance from which the sample was derived by calculation of an estimated coefficient of variation comprising a component due to statistical variation based upon the number of colonies used in estimating the bacterial concentration, a component associated with the quality measure of the subsample obtained from the distribution qualification and a component associated with the total corrected count derived from the count correction procedure.

16. The method of claim 15 wherein the estimated coefficient of variation is used for the purpose of qualifying subsamples and selecting among the subsamples those subsamples with data which is preferable in estimating the bacterial concentration of the deposited sample.

* * * * *